United States Patent [19]

Gregory et al.

[11] 4,014,869
[45] Mar. 29, 1977

[54] CEPHALOSPORIN DERIVATIVES

[75] Inventors: Gordon Ian Gregory, Chalfont St. Peter; Michael Gregson, London; Godfrey Basil Webb, Greenford, all of England

[73] Assignee: Glaxo Laboratories Limited, Greenford, England

[22] Filed: Dec. 2, 1974

[21] Appl. No.: 528,944

[30] Foreign Application Priority Data

Dec. 5, 1973 United Kingdom ............. 56460/73

[52] U.S. Cl. ........................ 260/240 J; 260/240 R; 260/243 C; 424/246
[51] Int. Cl.$^2$ ...................................... C07D 501/20
[58] Field of Search ......... 260/243 C, 240 R, 240 J
[56] References Cited
UNITED STATES PATENTS 3,453,272  7/1969  Talrano et al. ................ 260/243 C Primary Examiner—Nicholas S. Rizzo
Assistant Examiner—D. B. Springer
Attorney, Agent, or Firm—Bacon & Thomas

[57] ABSTRACT

Novel antibiotic compounds which are 7β-acrylamidoceph-3-em-4-carboxylic acids, and 6β-acrylamidopenam-3-carboxylic acids and non-toxic derivatives thereof wherein the acrylamido group has the structure

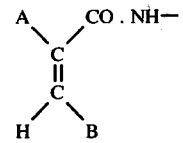

wherein A is aryl group and B is a substituted or unsubstituted lower alkyl, lower alkenyl or lower alkynyl group; or an aryl, cycloalkyl or cycloalkenyl group. These compounds possess antibacterial activity against gram-positive and gram-negative organisms coupled with stability to β-lactamases. The invention further relates to the administration of the compounds.

7 Claims, No Drawings

CEPHALOSPORIN DERIVATIVES

This invention is concerned with improvements in or relating to antibiotics of the cephalosporin and penicillin series.

As is well known, antibiotics of the cephalosporin and penicillin series are respectively 7β-acylamidoceph-3-em-4-carboxylic acids and 6β-acylamidopenam -3-carboxylic acids and their various non-toxic derivatives e.g. salts, esters, lactones (if such can be formed), amides, hydrates or the corresponding sulphoxides. In the cephalosporin series, these antibiotics may contain various substituents at the 3-position including unsubstituted methyl and methyl groups substituted with a variety of substituents as is described in the literature. In the penicillin series, substitution may, for example, be present on at least one of the gem-dimethyl groups.

The new compounds of the present invention are characterized in that said acylamido group of the cephalosporin or penicillin antibiotic is an α,β-disubstituted acrylamido group in which the β-substituent of the acryloyl group is cis- in configuration with respect to the carboxamido group. We have found the cis- compounds to have good antibacterial activity and in particular, markedly improved activity against gram negative organisms over the corresponding trans-compounds.

According to one embodiment of the invention therefore, we provide a compound selected from the group of 7β-acrylamidoceph-3-em-4-carboxylic acids (and non-toxic derivatives thereof) and 6β-acrylamidopenam-3-carboxylic acids (and non-toxic derivatives thereof) in which the acrylamido group has the structure:

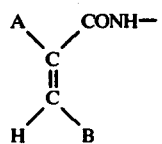

wherein A represents an aryl group and B represents a substituted or unsubstituted lower alkyl, lower alkenyl or lower alkynyl group; or an aryl, cycloalkyl or cycloalkenyl group. Whenever A and B are both aryl groups, these may be the same or different.

The compounds of the invention are defined as having the cis is opposed to the trans isomeric form as regards the configuration of the group B with respect to the carboxamido group. The stereochemical configuration around the double bond in the 7β-side-chain of the compounds of the invention, and of the αβ-disubstituted acrylic acids that are among the starting materials, can be unambiguously assigned in the E/Z nomenclature, such as is described in JACS, 90,509, (1968).

The compounds of the invention may be defined by the formula:

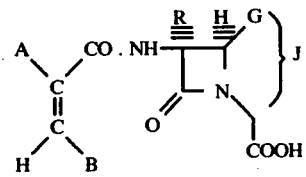

in which A and B are as defined above, G is > S or > S → O, J is a group in which 1 or 2 carbon atoms link the nuclear sulphur atom and the carbon atom bearing the carboxyl group and R is a hydrogen atom or a lower-alkythio or lower alkoxy group, having e.g. up to four carbon atoms.

The term "non-toxic" as applied to the derivatives of the compounds of the invention means those derivatives which ae physiologically acceptable in the dosage at which they are administered.

Salts which may be formed, where applicable, from the compounds according to the invention include (a) inorganic base salts such as alkali metal, e.g. sodium and potassium, alkaline earth metal e.g. calcium, and organic base, e.g. procaine, phenyl-ethylbenzylamine and dibenzylethylene diamine, salts and (b) acid addition salts e.g., with hydrochloric, hydrobromic, sulphuric, nitric, phosphoric, toluene-p-sulphonic and methane sulphonic acids. The salts may also be in the form of resinates, formed e.g., with a polystyrene resin containing amino, quaternary amino, or sulphonic acid groups, or a resin containing carboxyl groups e.g. a polyacrylic acid resin. The resin may if desired be cross-linked, e.g. it may be a copolymer of styrene and divinyl-benzene containing the appropriate groups.

Biologically acceptable esters which may be formed from the compounds according to the invention include those formed with alcohols of the formula $R^2.CO.O. CHR^1.OH$ 

wherein $R^1$ is hydrogen or lower alkyl and $R^2$ is hydrogen, lower alkyl, lower alkoxy, $C_5$-$C_7$ cycloalkyl, aryl e.g. phenyl, aralkyl e.g. benzyl, lower cycloalkylalkyl, 5- or 6-membered heterocyclic containing O, N or S, lower alkyl substituted by such heterocyclic group, or the group $-(CH_2)_n.CR^5R^6.NR^3R^4$ 

where $n$ is 0 or an integer of from 1–5, $R^3$, $R^4$ and $R^5$ are hydrogen or a lower alkyl group and $R^6$ is hydrogen, or a lower alkyl, lower alkoxy, lower carbalkoxy, aryl, 5- or 6-membered heterocyclic containing O, N or S or aralkyl group or any two of the groups $R^3$, $R^4$, $R^5$ and $R^6$ may together form a 5- or 6-membered ring with the adjacent N- or C- atom.

Such esters may also be formed with alcohols of the formula $CHR^7R^8OH$ 

where $R^7$ is hydrogen, $R^8$ may be lower alkanol, substituted or unsubstituted aroyl (carbocyclic or heterocyclic), cyano, lower alkylthio, lower alkoxy, aryloxy e.g. phenoxy, lower carbaloxy, carbobenzoxy, carbophenoxy, substituted or unsubstituted carbamoyl, lower alkyl sulphonyl, or substituted imino such as N-phthalimido and where $R^8$ is lower carbalkoxy, $R^7$ may be lower carbalkoxy and where $R^8$ is lower alkanoyl, $R^7$ may be lower alkyl.

The compounds of the invention, including the non-toxic derivatives thereof, are characterized by their antibacterial activity against a range of gram-positive and gram-negative organisms coupled with stability to β-lactamases produced by various gram-negative organisms.

Stability to β-lactamases may be assessed as compared with cephaloridine which may be arbitrarily defined as having a value of 1 with respect to the particular organism.

The cephalosporin compounds referred to in this specification are generally named with reference to cepham (J.Amer. Chem.Soc. 1962, 84 3400). The term "cephem" refers to the basic cepham structure with one double bond. The penicillin compounds referred to in this specification are generally named with reference to penam (J.Amer.Chem.Soc. 1953, 75, 3293).

The cephalosporin compounds according to the invention include compounds of the general formula

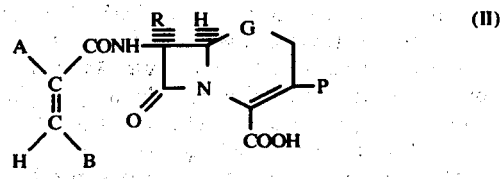

(wherein A, B, G and R have the above defined meanings, P is an organic group or a hydrogen, chlorine, bromine or fluorine atom) and non-toxic derivatives thereof.

The penicillin compounds according to the invention include compounds of the general formula

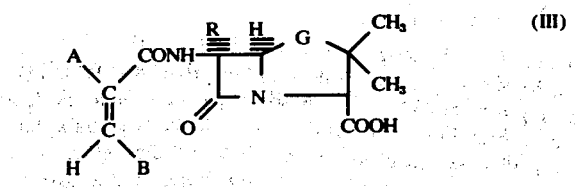

(wherein A, B, G and R have the above-defined meanings) and non-toxic derivatives thereof.

In formulae (II) and (III) G is preferably > S.

The invention also includes cephalosporin and penicillin compounds not specifically embraced by formulae II and III, e.g. 2β-acetoxymethyl penicillins and 2-methoxy and 2-methylthio cephalosporins.

The groups A and B (where B is aryl) in the above general formulae may be unsubstituted or substituted aryl (carbocyclic or heterocyclic) groups. Examples of these groups include phenyl; naphthyl; phenyl or naphthyl substituted by halo (e.g. chloro or bromo), hydroxy, lower alkyl (e.g. methyl), nitro, cyano, amino, lower alkylamino (e.g. methylamino), diloweralkylamino (e.g. dimethylamino), lower alkanoyl (e.g. acetyl), lower alkanoylamido, lower alkoxy (e.g. methoxy or ethoxy), lower alkylthio (e.g. methylthio), carboxy or carbalkoxy; a 5- or 6-membered heterocyclic group containing at least one hetero atom selected from S, N and O e.g. thien-2-yl, thien-3-yl, fur-2-yl, fur-3-yl, pyridyl, oxazolyl or isoxazolyl; oxadiazoyl or tetrazolyl.

The group B in the above formulae may also be chosen from alkyl, alkenyl or alkynyl groups of up to 7 carbon atoms, e.g. methyl, ethyl, propyl, vinyl, prop-1-enyl; or, for example, such a group substituted by an aryl, cycloalkyl or cycloalkenyl group, halogen (F, Cl, Br, I), alkoxy, acyloxy, carboxy or amino or substituted amino derivatives of such groups.

Where the group B is an alkyl, alkenyl, or alkynyl group substituted by an aryl group, the latter may be any of the aryl groups listed above for the groups A and B. Where the group B is similarly substituted by a cycloalkyl or cycloalkenyl group, the latter may be $C_3$-$C_7$.

The 3-substituent P of the above cephalosporin compounds may be any organic group, the characterising feature of the invention being the nature of the 7-substituent. P may thus be a saturated or unsaturated, substituted or unsubstituted, organic group containing 1–20 carbon atoms. Preferred saturated organic groups include methyl and ethyl; preferred unsaturated organic groups include vinyl and substituted vinyl groups of the formula

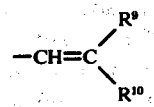

wherein $R^9$ and $R^{10}$, which may be the same or different, are each hydrogen or a substituted or unsubstituted aliphatic (e.g. alkyl, preferably $C_1$-$C_6$ alkyl such as methyl, ethyl, iso-propyl, n-propyl etc.), $C_5$-$C_7$ cycloaliphatic (e.g. cyclopentyl or cyclohexyl), $C_7$-$C_{10}$ araliphatic (e.g. benzyl or phenylethyl), $C_6$-$C_{12}$ aromatic (e.g. phenyl or nitrophenyl) group, nitrile or lower alkoxycarbonyl.

When P is a substituted methyl group it may be depicted by the formula

—$CH_2Y$ wherein Y is an atom or group e.g. the residue of a nucleophile or a derivative of a residue of a nucleophile. Y may thus, for example, be derived from the wide range of nucleophilic substances characterised by possessing a nucleophilic nitrogen, carbon, sulphur or oxygen atom described widely in earlier patents and literature pertaining to cephalosporin chemistry. Examples of such nucleophiles include:

NITROGEN NUCLEOPHILES

Examples of nitrogen nucleophiles include tertiary aliphatic, aromatic, araliphatic and cyclic amines including trialkylamines, for example, triethylamine, pyridine bases such as pyridine and alkyl pyridines; heterocyclinc amines having more than one heteroatom, at least one heteroatom being nitrogen, such as pyrimidines, purines, pyridazines, pyrazines, pyrazoles, imidazoles, triazoles and thiazoles.

A preferred class of nitrogen nucleophiles are those compounds of the formula:

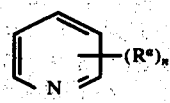

in which n is 0 or an integer from 1 to 5 and R$^a$, which when n is from 2 to 5, may be the same or different, is an aliphatic, e.g. lower alkyl such as methyl, ethyl, n-propyl, iso-propyl etc; an aryl e.g. phenyl; an araliphatic, e.g. phenyl lower alkyl such as benzyl, phenylethyl etc; or an alkoxymethyl e.g. methoxymethyl, ethoxymethyl, n-propoxymethyl, iso-propoxymethyl etc; or acyloxymethyl e.g. alkanoyloxymethyl such as acetoxymethyl; formyl; carbamoyl; acyloxy e.g. alkanoyloxy such as acetoxy; esterified carboxyl; alkoxy e.g. methoxy, ethoxy, n-propoxy, iso-propoxy etc; aryloxy e.g. phenoxy; aralkoxy e.g. benzyloxy; alkylthio e.g. methylthio, ethylthio; arylthio; aralkylthio; cyano; hydroxy; N-monoloweralkylcarbamoyl e.g. N-methylcarbamoyl, N-ethylcarbamoyl etc; N,N-diloweralkylcarbamoyl e.g. N,N-dimethylcarbamoyl, N,N-diethylcarbamoyl etc; N-(hydroxyloweralkyl)carbamoyl e.g. N-(hydroxymethyl)carbamoyl, N-(hydroxyethyl)carbamoyl etc; or carbamoylloweralkyl e.g. carbamoylmethyl, carbamoylethyl etc. group.

Another prefered class of nitrogen nucleophiles are azides e.g. alkali metal azides such as sodium azide.

When the group Y is a derivative of a residue of a nucleophile it may be an amino group or an acylamido group. Compounds in which Y is amino may be derived from the corresponding azide by reduction e.g. by catalytic hydrogenation of the azide using a precious metal catalyst such as palladium or platinum.

The amino group may be acylated to form a corresponding 3-acylaminomethyl compound. The formation of such compounds may, for example, be effected by any method suitable for acylating an aminocephalosporin e.g. reaction of the 3-aminomethyl compound with an acid chloride, acid anhydride or mixed anhydride or an acid corresponding to the desired acyl group and another acid.

The 3-aminomethyl compounds may also be reacted with a substituted isocyanate or isothiocyanate to yield urea or thiourea derivatives.

Other compounds in which Y is a derivative of a residue of a nucleophile may be obtained by reacting 3-azidomethyl compounds with a dipolarophile. Preferred classes of dipolarophiles include acetylenic, ethylenic and cyano dipolarophiles.

Acetylenic dipolarophiles may be shown as having the structure

wherein R$^{11}$ and R$^{12}$ which may be the same or different are atoms or groups.

In general we prefer that R$^{11}$ and preferably also R$^{12}$ should be of an electronegative nature. Examples of such groups include cyano, CO$_2$R$^{13}$, COR$^{13}$ (where R$^{13}$ is for example, lower alkyl, aryl or lower aralkyl), and trihalomethyl e.g. trifluoromethyl.

However, R$^{11}$ and preferably also R$^{12}$ could be electropositive e.g. alkoxy or alkylamino.

R$^{11}$ and R$^{12}$ may together form a ring system with the acetylenic group such as, for example, in an aryne.

Where R$^{11}$ and R$^{12}$ are discrete atoms or groups which are identical a single compound will result on reaction with the azido cephalosporin; if they are different one will in general obtain a mixture of position isomers.

Ethylenic dipolarophiles may be shown as having the structure

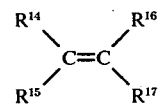

where R$^{14}$, R$^{15}$, R$^{16}$ and R$^{17}$ which may be the same or different are atoms or groups. Although R$^{14}$, R$^{15}$, R$^{16}$ and R$^{17}$ may all be hydrogen, ethylene per se, like acetylene, reacts sluggishly with azido groups. R$^{14}$ and R$^{16}$ may together form a cyclic structure, e.g. a carbocyclic structure, with the ethenoid group such that the double bond is strained. Examples of ethylenic dipolarophiles containing strained double bonds include norbornenes, transcycloalkenes and acenaphthalene.

Further ethylenic dipolarophiles which may be used include compounds of the formula R$^{14}$.R$^{15}$.C = CR$^{16}$.R$^{17}$ where at least one of R$^{14}$, R$^{15}$, R$^{16}$ and R$^{17}$ is an electronegative group. R$^{14}$ and R$^{16}$ may thus be identical electronegative groups, R$^{15}$ and R$^{17}$ being other groups as desired. R$^{15}$ and R$^{17}$ may thus together form a ring system. Examples of such dipolarophiles include benzoquinone and nuclear substituted benzoquinones and malemide. Again all of R$^{14}$, R$^{15}$, R$^{16}$ and R$^{17}$ may be identical electronegative groups. Electronegative groups which may be used include those listed under the section on acetylenic dipolarphiles and examples of such compounds thus include dicyanoethylene and lower mono- and di-alkoxycarbonyl ethylenes.

One or more of R$^{14}$, R$^{15}$, R$^{16}$ and R$^{17}$ may if desired be electropositive.

Cyano compounds, especially those which are activated by electronegative groups, may function as cyano dipolarophiles. Examples of such dipolarophiles include lower alkoxy carbonyl cyanides and cyanogen.

CARBON NUCLEOPHILES

Examples of "carbon nucleophiles" include inorganic cyanides, pyrroles and substituted pyrroles, e.g. indoles, and compounds giving stabilised carbanions, for example, acetylenes and compounds having β-diketone groups, for example acetoacetic and malonic esters and cyclohexane-1,3-diones or enamines, ynamines or enols.

The carbon nucleophile may thus give rise to cephalosporin compounds characterized by possessing a substituent at the 3-position in which a carbonyl group is linked to the cephalosporin nucleus through two carbon atoms. Such compounds may thus possess as the 3-substitutent a group of the formula

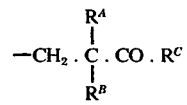

wherein R$^A$ and R$^B$, which may be the same or different, are selected from hydrogen, cyano, lower alkyl e.g. methyl or ethyl, phenyl, substituted phenyl e.g. halo, lower alkyl, lower alkoxy, nitro, amino or lower alkylamino phenyl, lower alkoxycarbonyl, mono- or di-aryl lower alkoxycarbonyl, lower alkylcarbonyl, aryl lower alkyl or C$_5$ or C$_6$ cycloalkyl and R$^C$ is selected from hydrogen, lower alkyl e.g. methyl or ethyl, phenyl, substituted phenyl e.g. halo, lower alkyl, lower alkoxy, nitro, amino or lower alkylamino phenyl, aryl lower alkyl or C$_5$ or C$_6$ cycloalkyl.

SULPHUR NUCLEOPHILES

Examples of "sulphur nucleophiles" include thiourea and aliphatic, aromatic, araliphatic, alicyclic and heterocyclic substituted thioureas; dithiocarbamates; aromatic, aliphatic and cyclic thioamides, for example thioacetamide and thiosemicarbazide; thiosulphates, thiols; thiophenols; thioacids, e.g. thiobenzoic acid or thiopicolinic acid; and dithioacids.

A preferred class of "sulphur nucleophile" includes those compounds of the formula: $R^D.S(O)_nH$ in which $R^D$ is an aliphatic e.g. lower alkyl such as methyl, ethyl, n-propyl etc. group; an alicyclic e.g. cyclohexyl, cyclopentyl etc. group; an aromatic e.g. phenyl, naphthyl etc. group; an araliphatic e.g. benzyl group; or a heterocyclic group, and $n$ is 0, 1 or 2. A particularly preferred class of nucleophiles falling within the above formula is that having the general formula: $R^E$ SH in which $R^E$ is an aliphatic e.g. lower alkyl e.g. methyl ethyl, n-propyl etc.; araliphatic, e.g. phenyl lower alkyl e.g. benzyl, phenylethyl etc. or substituted phenyl lower alkyl; alicyclic e.g. cycloalkyl e.g. cyclopentyl or cyclohexyl; aromatic e.g. phenyl or substituted phenyl or a 5- or 6-membered heterocyclic group containing at least one of O, N and S e.g. thiadiazolyl particularly 5-methyl-1,3,4-thiadiazol-2-yl, diazolyl, triazolyl, tetrazolyl, thiazolyl, thiatriazolyl, oxazolyl, oxadiazolyl, benzimidazolyl, benzoxazolyl, benthiazolyl, triazolopyridyl, purinyl, pyridyl, pyrimidyl, etc.

OXYGEN NUCLEOPHILES

Examples of oxygen nucleophiles include water, alcohols, for example alkanols such as methanol, ethanol, propanol and butanol and lower alkanoic acids, eg acetic acid.

The term "oxygen nucleophile" thus includes compounds of the following formula:

$$R^b OH$$

in which the group $R^b$ may be lower alkyl (e.g. methyl, ethyl, n-propyl, isopropyl, n-butyl, isobutyl etc.); lower alkenyl (e.g. allyl); lower alkynyl (e.g. propynyl, etc); lower cycloalkyl (e.g. cyclopentyl, cyclohexyl, etc); lower cycloalkyl lower alkyl (e.g. cyclopentylmethyl, cyclohexylethyl etc); aryl (e.g. phenyl or naphthyl); aryl lower alkyl (e.g. benzyl); heterocyclic; heterocyclic lower alkyl (e.g. furfuryl), or any of these groups substituted by, for example, one or more of lower alkoxy (methoxy, ethoxy, etc.), lower alkylthio (methylthio, ethylthio, etc), halogen (chlorine, bromine, iodine or fluorine), lower alkyl (methyl, ethyl etc), nitro, hydroxy, acyloxy, carboxy, carbalkoxy, lower alkylcarbonyl, lower alkylsulphonyl, lower alkoxysulphonyl, amino, lower alkylamino or acylamino groups. Another example of an oxygen nucleophile occurs where $R^b$ is a carbamoyl group. The latter may be mono- or di-substituted with a lower alkyl group.

In the case in which water is the nucleophile there will be obtained 3-hydroxymethyl cephalosporin compounds. Such compounds have the formula

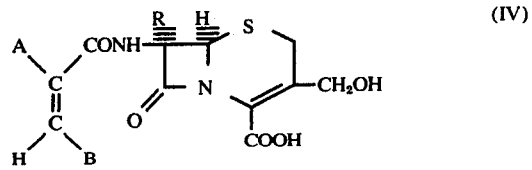

where A, B and R have the above defined meanings. Compounds of formula (IV) are metabolites of compounds of general formula (II) where P is acyloxymethyl Compounds of formula (IV) may be acylated to form derivatives characterised by possessing the group 3-$CH_2.O.CO.R^d$ or 3-$CH_2.O.CO.QR^d$ where Q is O, S or NH in which $R^d$ is hydrogen, methyl or an organic group having an atomic weight sum of at least 16.

The group $R^dCO$- or, $R^dQ.CO$- may be chosen from among the wide class of such groups described to the literature and may have up to 20 carbon atoms. The group $R^d$ may thus be a hydrocarbon group or such a group carrying one or more substituent atoms or groups. The group $R^d$ may thus be chosen from the following list which is not intended to be exhaustive:

(i). $C_nH_{2n+1}$ where $n$ is an integer from 1 to 7, e.g. 1 to 4, for example methyl. The group may be straight or branched and, if desired, may be interrupted by an oxygen or sulphur atom or an imino group or substituted by cyano, carboxy, alkoxycarbonyl, hydroxy, carboxycarbonyl (HOOC.CO.), halogen e.g. chlorine, bromine or iodine, or amino. Examples of such groups include ethyl, propyl, isopropyl, n-butyl, t-butyl or sec.-butyl (ii). $C_nH_{2n-1}$ where $n$ is an integer from 2 to 7. The group may be straight or branched and, if desired, may be interrupted by an oxygen or sulphur atom or an imino group. An example of such a group is vinyl or propenyl, (iii). $R^e$, where $R^e$ is aryl (carbocyclic or heterocyclic), cycloalkyl, substituted aryl and substituted cycloalkyl. Examples of this group include phenyl; substituted phenyl e.g. hydroxyphenyl, chlorophenyl, fluorophenyl, tolyl, nitrophenyl, aminophenyl, methoxyphenyl or methylthiophenyl; thien-2- and -3-yl; pyridyl; cyclohexyl; cyclpentyl; sydnone; naphthyl; substituted naphthyl e.g. 2-ethoxynaphthyl, (iv). $R^e(CH_2)_m$ where $R^e$ has the meaning defined above under (iii) and $m$ is an integer from 1 to 4. Examples of this group include methyl, ethyl or butyl substituted by the various specific $R^e$ groups listed under (iii) e.g. benzyl and the appropriate substituted benzyl groups.

An important class of cephalosporin compounds are those possessing the group 3-$CH_2Hal$ wherein Hal is chlorine, bromine or iodine. Such compounds may be primarily of value as intermediates of use in the preparation of active cephalosporin compounds.

Preparation

The compounds according to the invention may be prepared by any convenient method. According to one embodiment of the invention we provide a process for the preparation of a compound of the formula

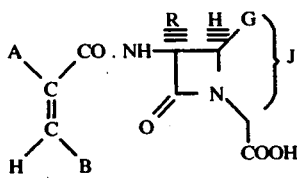
(I)

(wherein A and B are as hereinbefore defined, G is > S or > S → O, J is a group in which 1 or 2 carbon atoms link the nuclear sulphur atom and the carbon atom bearing the carboxyl group) and R is a hydrogen atom or a lower alkylthio or lower alkoxy group having e.g up to 4 carbon atoms, and derivatives thereof, which comprises either (a) condensing a compound of the formula

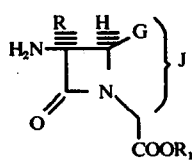
(V)

(wherein R, G and J have the above defined meanings and $R_1$ is hydrogen or a carboxyl blocking group) with an acylating agent, corresponding to the acid

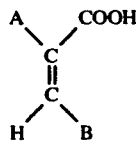
(VI)

(wherein A and B have the above defined meanings) and the group B has the cis- configuration with respect to the carboxyl group, or (b) reacting a compound of the formula

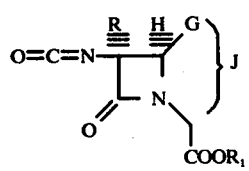
(VII)

(wherein R, G, J and $R_1$ have the above defined meaning except that $R_1$ is not hydrogen) with an acid of formula (VI) or (c), where J is the group

(wherein P is a hydrogen, chlorine, bromine or fluorine atom or a group —$CH_2Y$, where Y is the residue of a nucleophile or a derivative of the residue of a nucleophile and the dotted line bridging the 2, 3 and 4 positions indicates that the compound may be a ceph-2-em or a ceph-3-em compound) reacting a compound of the formula

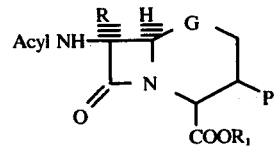

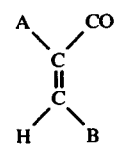

G, A, B,R,$R_1$ and the dotted line have the above meanings and P is a hydrogen, chlorine, fluorine or bromine atom or a group —$CH_2Y^1$, wherein $Y^1$ is a replaceable residue of a necleophile) with a nucleophile whereafter if necessary and desired in each instance, any of the following reactions (d) are carried out (i) conversion of a $\Delta^2$ isomer into the desired $\Delta^3$ isomer (ii) removal of any carboxyl blocking groups (iii) reduction of a compound in which G is >S → O to form the desired G =>S compound (iv) reduction of a compound in which Y is azide to form a 3-aminomethyl compound (v) reaction of a compound in which Y is azide with a dipolarophile to form a compound having a polyazole ring linked to the 3-methylene group (vi) deacylation of a compound in which Y is an acyloxy group to form a 3-hydroxymethyl compound and (vii) acylation of a compound in which Y is hydroxy to form a 3-acyloxymethyl or 3-carbamoyloxymethyl compound and (e) recovering the desired compound of formula (I), if necessary, after separation of isomers.

Salts of the compounds according to the invention may be formed in any convenient way. For example base salts may be formed by reaction of the penicillin or cephalosporin acid with sodium or potassium 2-ethylhexanoate.

In practice it is convenient to condense an acylating agent corresponding to the acid

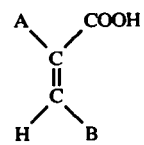
(VI)

where A and B have the above defined meanings, with an amino compound

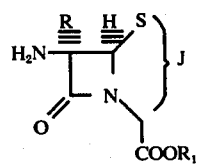
(VIII)

[where R and J have the above defined meanings and $R_1$ is hydrogen or a carboxyl blocking group e.g. the residue of an ester-forming alcohol (aliphatic or araliphatic), phenol, silanol, stannanol or acid] the condensation, if desired, being effected in the presence of a condensation agent, and being followed, if necessary, by removal of the group $R_1$.

In the case of the preparation of cephalosporin and penicillin compounds the amino compound (VIII) may correspond to compounds (II) and (III) above and have the formulae

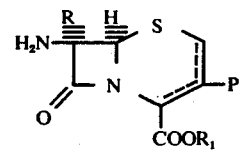 (IX)

and

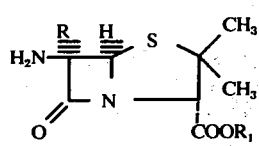 (X)

respectively, wherein R, $R_1$, and P and the dotted line have the above defined meanings. There may also be used a derivative of the amino compounds such as a salt e.g. a tosylate. The acylation may be effected at temperatures of from $-50$ to $+50°$ C, preferably from $-20°$ to $+20°$ C e.g. about $0°$ C. The acylating agent may be prepared by reacting the acid (VI) with a halogenating agent e.g. phosphorus pentachloride, thionyl chloride or oxalyl chloride. Use of oxalyl chloride with the sodium, potassium, triethylamine or dimethylaniline salt of the acid VI is advantageous. The acylation may be effected in aqueous or non-aqueous media and suitable media include an aqueous ketone such as aqueous acetone, an ester e.g. ethyl acetate, or an amide e.g. dimethylacetamide, or a nitrile e.g. acetonitrile, or a halogenated hydrocarbon e.g. methylene dichloride, or mixtures thereof.

Acylation with an acid halide may be effected in the presence of an acid binding agent e.g. a tertiary amine (e.g. triethylamine or dimethylaniline), an inorganic base (e.g. calcium carbonate or sodium bicarbonate) or an oxirane, which binds hydrogen halide liberated in the acylation reaction. The oxirane is preferably a lower-1, 2-alkylene oxide e.g. ethylene oxide or propylene oxide.

When using the free acid form of a compound of formula (VI), suitable condensing agents for use in the preparation of the compounds according to the invention include carbodiimides, for example N,N'-diethyl-, dipropyl- or diisopropylcarbodiimide, N,N'-dicylohexylcarbodiimide, or N-ethyl-N'-γ-dimethylaminopropylcarbodiimide; a suitable carbonyl compound, for example carbonyldiimidazole; or an isoxazolinium salt, for example, N-ethyl-5-phenylisoxazolinium-3'-sulphonate and N-t-butyl-5-methylisoxazolinium perchlorate. The condensation reaction is desirably effected in an anhydrous reaction medium, e.g. methylene chloride, dimethylformamide or acetonitrile, since one may then regulate more precisely reaction parameters such as temperature.

Alternatively, acylation may be effected with other amide-forming derivatives of the free acid such as, for example, a symmetrical anhydride or mixed anhydride, e.g. with pivalic acid or formed with a haloformate, e.g. a lower alkylhaloformate. The mixed or symmetrical anhydrides may be generated in situ. For example, a mixed anhydride may be generated using N-ethoxycarbonyl-2-ethoxy-1, 2-dihydroquinoline. Mixed anhydrides may also be formed with phosphorus acids (for example phosphoric or phosphorous acids), sulphuric acid or aliphatic or aromatic sulphonic acids (for example p-toluene sulphonic acid).

Alternatively the compound of formula (I) may be prepared from a compound of formula

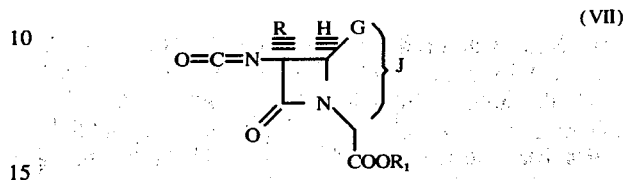 (VII)

where R, G, J and $R_1$ have the above defined meanings (except $R_1=H$) by reaction with an acid of formula (VI) and subsequently removing the group $R_1$.

The reaction involving the use of a compound of formula (VIII) or (VII) may be carried out towards the end of the preparative sequence, the only additional reactions being deprotection reactions and purifications.

If desired the replacement of one P group by another and preferred P group may be carried out after acylation of the 7-amino compound has taken place. In particular when P is the group $-CH_2Y$ where Y has the above defined meaning the Y group may be introduced by methods described in the literature. Thus compounds in which Y is a halogen atom, an ether group, or a thioether group may be prepared as described in Belgian Patents Nos. 719,711; 719,710; 734,532 and 734,533. Compounds wherein Y is the residue of a nucleophile may also be prepared by the reaction of a 3-acetoxymethyl cephalosporin compound with a nucleophile, for example, pyridine or other tertiary amine as described in British Patent No. 912,541; a sulphur-linking, nitrogen-linking or inorganic nucleophile as described in British Patent No. 1,012,943; a sulphur-linking nucleophile as described in British Patents 1,206,305; 1,059,562, 1,101,423 and 1,206,305; or a nitrogen-linking nucleophile as described in British Patents Nos. 1,030,630, 1,082,943 and 1,082,962.

Compounds in which Y is a derivative of a residue of a nucleophile such as an amino or acylamido group derived from an azido group and compounds in which Y is azido and is reacted with a dipolarophile may be prepared as described in British Patents Nos. 1,057,883 and 1,211,694. Compounds of the invention wherein Y is the residue of a nucleophile may also be prepared by the reaction of a 3-halomethyl-cephalosporin with any of the nucleophiles disclosed in the above references, such a process being described in Belgian Patent No. 719,711. Where Y is a hydroxy group the compound may be prepared by the methods described in British Patent No. 1,121,308.

Compounds having a vinyl or substituted vinyl group as 3-position substituent may be obtained by the method described in Belgian Patent No. 761,897.

Where Y is a halogen (i.e. chlorine, bromine or iodine) ceph-3-em starting compounds may be prepared by halogenation of a 7β-acylamido-3-methylceph-3-em-4-carboxylic acid ester 1β-oxide followed by reduction of the 1β-oxide group later in the sequence as described in Belgian Patent No. 755,256.

Where Y is a carbamoyloxy group, this (and precursors thereof) may be introduced by conventional methods. Thus, for example, a 3-hydroxymethyl cephalosporin may be reacted with an isocyanate of formula $R^c$.NCO (wherein $R^c$ represents a labile substituent group or an alkyl group) to give a compound containing a group P of formula —$CH_2O.CO.NHR^c$ (where $R^c$ has the above defined meaning) at the 3-position; such groups may, if desired, and if $R^c$ is labile, be converted to a 3-carbamoyloxymethyl group by subsequent cleavage of the group $R^c$, e.g. by hydrolysis. Labile groups $R^c$ which are readily cleavable upon such subsequent treatment include chlorosulphonyl and bromosulphonyl (see German OLS 2,203,653); aralkyl groups such as benzyl, p-methoxybenzyl and diphenylmethyl; lower alkyl groups such as t-butyl; and halogenated lower alkanoyl groups such as dichloroacetyl and trichloroacetyl; and halogenated lower alkanoyl group such as 2,2,2-trichloroethoxycarbonyl.

The corresponding ceph-2-em compounds may be prepared by the method of Dutch published Patent Application No. 6902013 by reaction of a ceph-2-em-3-methyl compound with N-bromo-succinimide to yield the ceph-2-em-3-bromomethyl compound.

Where Y is a hydrogen atom the compound may be prepared by the method described in British Patent No. 957,569 or from a penicillin compound by the method described in U.S. Pat. Specification No. 3,275,626 and Belgian Patents Nos. 747,119 and 747,120.

Cephalosporin compounds possessing an acyloxymethyl group as 3-position substituent may be prepared by any convenient method e.g. they may be prepared from a cephalosporin having a 3—$CH_2Y$ group where Y = OH or the residue of the acid HY which has a pKa of not more than 4.0 and preferably not more than 3.5 (as measured in water at 25° C).

The group Y may be a chlorine, bromine or iodine atom, formyloxy or an acetoxy group having at least one electron withdrawing substituent on the α-carbon atom or a nuclear substituted benzoyloxy group, the nuclear substituent being of the electron withdrawing type as described in British Patent No. 1,241,657 and the nucleophilic displacement reaction to introduce the desired 3-position substituent may be carried out as described in our aforesaid British Patent No. 1,241,657.

Alternatively where Y is hydroxy the desired 3-acyloxymethyl cephalosporin may be obtained by acylation as described in British Patent No. 1,141,293. In British Patent No. 1,141,293 there is described a process for the preparation of a $\Delta^3$-cephalosporin having a 3-acyloxymethyl substituent from a corresponding 3-hydroxymethyl analogue which comprises aralkylating the 4-carboxy group, acylating the 3-hydroxymethyl group of the protected compound and subsequently removing the aralkyl group.

The group R may be a hydrogen atom or a lower alkylthio or alkoxy group having e.g. up to 4 carbon atoms. When R is an alkoxy group or alkylthio group, the compounds of formula I may either be prepared by the acylation of a compound of formula (VIII) wherein R is an alkoxy or alkylthio group, or else by direct introduction of the group R into the compound of formula I. The preparation of the compounds of formula (VIII) and formula (I) wherein R is other than hydrogen is described in Belgian Patent No. 768528, or Dutch Published Patent Application No. 7204982 and may also be effected by techniques involving the N-deacylation of fermentation-produced 7β-acylamido-7α-alkoxy cephalosporins or the ring expansion of 6α-alkoxypenicillin sulphoxides. Other methods are also described in J.AM.Chem.Soc. 1973, 95 2401-3 and 2403-4 and in J.Org.Chem, 1973, 38, 2857 and Tetrahedron Letters 1973, No.4, 273-6.

Compounds of formula II in which P is hydrogen or fluorine, chlorine or bromine are desirably prepared by the process of the invention using a starting material of formula (IX) which, when P is hydrogen, may be prepared by a method as described in Belgian Patent No. 774,480 or French Patent. No. 2165834 or which, when P is chlorine, bromine or fluorine may be prepared by a method as described in German OLS No. 2408686.

The acylation may be carried out by any convenient method using for example an acid chloride, acid anhydride or a mixed acid anhydride as the acylating agent preferably in the presence of an organic base such as pyridine and carrying out the reaction in solution in an inert anhydrous solvent for example methylene chloride. Alternatively the acylation may be carried out in aqueous acetone/sodium bicarbonate solution. The preferred acylating agent is the acid chloride.

The acylation reaction should be effected as rapidly as possible, since under the conditions of the acylation rearrangement to the $\Delta^2$-derivative can occur, particularly when an aroyloxy group is being introduced at the exocyclic methylene group at the 3-position.

Compounds of the formula (VIII) may be employed as esters; those of formula (VII) are esters. One may also use the free amino acid or an acid addition salt of the free amino acid or ester thereof. Salts which may be used include acid addition salts e.g. with hydrochloric, hydrobromic, sulphuric, nitric, phosphoric, toluene-p-sulphonic and methane sulphonic acids.

The ester may be formed with an alcohol, phenol, silanol or stannanol having up to 20 carbon atoms which may readily be split off at a later stage of the overall reaction.

Any esterifying group substituting the 4-carboxyl group of a compound of formula (VIII) or (VII) is preferably formed with an alcohol (aliphatic or araliphatic phenol, silanol, stannanol or acid which may readily be split off at a later stage of the reaction.

Suitable esters thus include compounds containing as ester group a group selected from the following list which is not intended to be an exhaustive list of possible ester groups. (i) — $COOCR_aR_bR_c$ wherein at least one of $R_a$, $R_b$ and $R_c$ is an electron-donor e.g. p-methoxyphenyl, 2,4,6-trimethylphenyl, 9-anthryl, methoxy, acetoxy, or fur-2-yl. The remaining $R_a$, $R_b$ and $R_c$ groups may be hydrogen of organic substituting groups. Suitable ester groups of this type include p-methoxybenzyloxycarbonyl and 2,4,6-trimethylbenzyloxy carbonyl. (ii) — $COOCR_aR_bR_c$ wherein at least one of $R_a$, $R_b$ and $R_c$ is an electron-attracting group e.g. benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniumethyl, o-nitrophenyl or cyano. The remaining $R_a$, $R_b$, and $R_c$ groups may be hydrogen or organic substituting groups. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl. (iii) — COO- $CR_aR_bR_c$ wherein at least two of $R_a$, $R_b$ and $R_c$ are hydrocarbon such as alkyl e.g. methyl or ethyl, or aryl e.g. phenyl and the remaining $R_a$, $R_b$ and $R_c$ group, if there is one, is hydrogen. Suitable esters of this type include t-butyloxycarbonyl, t-amyloxycarbonyl, diphenylmethoxycarbonyl and triphenylmethoxycarbonyl. (iv) — $COOR_d$ wherein $R_d$ is adamantyl, 2-benzyloxyphenyl, 4-methylthiophenyl, tetrahydrofur-2-yl or tetrahydropyran-2-yl. (v) Silyloxycarbonyl groups obtained by reaction of a carboxyl group with a derivative of a silanol. The derivative of a silanol is conveniently a halosilane or a silazane of the formula $R^F_3SiX$; $R^F_2SiX_2$; $R^F_3Si.NR^F_2$; $R^F_3Si.NH.SiR^F_3$; $R^F_3Si.NH.COR^F$; $R^F_3Si.NH.CO.NH.SiR^F_3$; $R^FNH.CO.NR^F.SiR^F_3$; or $R^FC(OSiR^F_3)$: $NSiR^F_3$ where X is a halogen and the various groups $R^F$, which can be the same or different, represent hydrogen atoms or alkyl, e.g. methyl, ethyl, n-propyl, iso-propyl; aryl, e.g. phenyl; or aralkyl e.g. benzyl groups. Preferred derivatives of silanols are silyl chlorides such as for example trimethylchlorosilane and dimethyldichlorosilane.

The carboxyl group may be regenerated from an ester by any of the usual methods, for example, acid- and base-catalysed hydrolysis is generally applicable, as well as enzymically-catalysed hydrolyses; however, aqueous mixtures may be poor solvents for these compounds and they may cause isomerizations, rearrangements, side-reactions, and general destruction, so that special methods may be desirable. Five suitable methods of deesterification are (1) Reactions with Lewis acids.

Suitable Lewis acids for reaction with the esters include trifluoroacetic acid, formic acid, hydrochloric acid in acetic acid, zinc bromide in benzene and aqueous solutions or suspensions of mercuric compounds. The reaction with the Lewis acid may be facilitated by addition of a nucleophile such as anisole. (2) Reduction.

Suitable systems for effecting reduction are zinc/acetic acid, zinc/formic acid, zinc/lower alcohol, zinc/pyridine, palladised-charcoal and hydrogen, and sodium and liquid ammonia. (3) Attack by nucleophiles.

Suitable nucleophiles are those containing a nucleophilic oxygen or sulphur atom for example alcohols, mercaptans and water. (4) Oxidative methods, for example, those which involve the use of hydrogen peroxide and acetic acid. (5) Irradiation.

Where at the end of a given preparative sequence compounds are obtained wherein G is > S → O and a compound is desired in which G is > S conversion to a sulphide may for example, be effected by reduction of the corresponding acyloxysulphonium or alkyloxysulphonium salt prepared in situ by reaction with e.g. acetyl chloride in the case of an acetoxysulphonium salt, reduction being effected by, for example, sodium dithionite or by iodide ion as in a solution of potassium iodide in a water miscible solvent e.g. acetic acid, tetrahydrofuran, dioxan, dimethylformamide or dimethylacetamide. The reaction may be effected at a temperature of −20° to +50° C.

Alernatively, reduction of the 1-sulphinyl group may be effected by phosphorus trichloride or tribromide in solvents such as methylene chloride, dimethylformamide or tetrahydrofuran, preferably at a temperature of −20° C to +50° C.

Where the resultant compound is a ceph-2-em-4-ester the desired ceph-3-em compound may be obtained by treatment of the former with a base.

Many of the acrylic acids of formula (VI) used in the preparation of the compounds of the invention are new compounds. Several convenient methods for the synthesis of these $\alpha\beta$-disubstituted acrylic acids exist. These are general methods which usually result in a mixture of cis- and trans- isomers which require separation.

One method, for example, involves the base-catalysed condensation of an aldehyde of formula B-CHO with a substituted acetic acid or a precursor or derivative thereof A $CH_2$ M, wherein A and B are as defined above and M may be a carboxy, carboloweralkoxy or cyano group. Reaction may be effected in a solution in acetic anhydride containing base e.g. triethylamine, using approximately equivalent quantities of the starting materials and the mixture of isomeric products may be isolated and purified using conventional separation techniques. Separation of the isomers may be achieved by crystallisation, and if the product is a derivative of a cis-$\alpha\beta$ disubstituted acrylic acid, the free acid may be obtained by hydrolysis and purification.

Another method involves the reaction between an $\alpha$-ketocarboxylic acid derivative, of the formula A CO.COL where A is as defined above and L is a lower e.g. $C_{1-7}$ alkoxy group, and a Wittig reagent of the type B-CH = $PAr_3$ wherein B is as defined above and Ar is an aryl e.g. a phenyl group. In this method, the Wittig reagent is generated from a phosphonium salt in an inert solvent by treating with a solution of a base, e.g. n-butyllithium, in an inert solvent such as a hydrocarbon and/or tetrahydrofuran or dioxan under an inert atmosphere e.g. of nitrogen, with cooling. The mixture resulting may then be reacted with the $\alpha$-ketocarboxylic acid derivative in an inert solvent. The isomeric acrylic acid derivatives in the residue may then be separated chromatographically or by selective hydrolysis and the cis- isomer hydrolysed to yield the cis-acid.

A third method involves the reaction of an aldehyde BCHO, where B is as defined above, with the anion derived from a phosphonic acid ester derivative such as may be prepared from an $\alpha$-haloarylacetic acid derivative A CH(Hal)COL, by reaction with trialkyl phosphite; wherein A and L are as defined above. Reaction of the phosphonic acid derivative A CH[P(O)(OAlk)_2] COL, wherein Alk is an alkyl group, desirably an ethyl group, in the presence of a strong base with an aldehyde compound B-CHO yields a mixture of isomeric products which may be separated chromatographically. Hydrolysis of the cis derivative yields the cis- acid.

A further method involves the treatment of a $\gamma$-lactone of formula

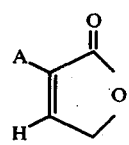

(XI)

wherein A is as defined above, with an alkylating or acylating agent under alkaline conditions. Suitable alkylating agents may include dialkylsulphates, e.g. dimethyl or diethyl sulphate, and suitable acylating agents include acid chlorides or acid anhydrides, e.g. acetic anhydride. This method generally provides acrylic acids of formula (VI) wherein B is an alkyl group substituted) by an alkoxy or acyloxy group.

Cis- and trans- isomers may be distinguished by appropriate techniques, e.g. by their ultraviolet spectra, by thin layer or paper chromatography or by their nuclear magnetic resonance spectra.

The antibacterial compounds according to the invention may be formulated for administration in any convenient way, by analogy with other antibiotics and the invention therefore includes within its scope a phamaceutical composition comprising an antibacterial compound of formula I or a non-toxic derivative e.g. salt thereof (as herein defined) adapted for use in human or veterinary medicine. Such compositions may be presented for use in conventional manner with the aid of any necessary pharmaceutical carriers or excipient.

The antibacterial compounds according to the invention may be formulated for injection and may be presented in unit dose form in ampoules, or in multidose containers with an added preservative. The compositions may take such forms as suspensions, solutions, emulsions in oily or aqueous vehicles, and may contain formulatory agents such as suspending, stabilising and/or dispersing agents. Alternatively the active ingredient may be in powder form for reconstitution with a suitable vehicle, e.g. sterile, pyrogen-free water, before use.

The composition may also be prepared in suitable forms for absorption through the mucous membranes of the nose and throat or bronchial tissues and may conveniently take the form of powder or liquid sprays or inhalants, lozenges, throat paints etc. For medication of the eyes or ears, the preparations may be presented as individual capsules, in liquid or semi-liquid form, or may be used as drops etc. Topical applications may be formulated in hydrophobic or hydrophilic bases as ointments, creams, lotions, paints, powders etc.

For veterinary medicine the composition, may, for example, be formulated as an intramammary preparation in either long acting or quick-release bases.

The compositions may contain from 0.1% upwards, preferably from 10–60% of the active material, depending on the method of administration. Where the compositions comprise dosage units, each unit will preferably contain 50–500 mg. of the active ingredient. The dosage as employed for adult human treatment will preferably range from 100–3000 mg. for instance 1500 mg per day, depending on the route and frequency of administration.

The compounds according to the invention may be administered in combination with other therapeutic agents such as antibiotics, for example other cephalosporins, the penicillins or tetracyclines.

The following preparations describe the synthesis of various starting materials used in the preparation of compounds of the invention. The Examples should not be construed as limiting the invention. Throughout all the Preparations and Examples, temperatures are in ° C.

Preparation 1

2-Phenyl-3-thien-2-ylpropenoic acid (cis isomer)

Methyl α-(diethylphosphono) phenyl acetate (Blicke and Raines, J. Org. Chem., 1964, 29 2036)(22.9 g.) in dry 1,2-dimethoxyethane (100 ml.) was treated at room temperature with sodium hydride powder (2 g.). The resulting mixture was stirred at room temperature for 4 hr. and at 60° for 1 hr. The solution, at 40°, was treated with thiophene-2-aldehyde (8.26 ml.) for 1 hr. The solvent was partially removed by evaporation and the residue added to water and extracted with ether. The ether extract was washed successively with aqueous sodium hydrogen carbonate solution, dilute hydrochloric acid and water and dried. Evaporation gave cis and trans isomeric mixture of methyl 2-phenyl-3-thien-2°-ylpropenoate as a pale yellow oil (19 g.). Crystallisation from cyclohexane gave (E)-methyl 2-phenyl-3-thien-2'-ylpropenoate as pale green crystals (3.68 g.) m.p. 78°–80°, $\lambda_{max}$. (EtOH) 233.5, 316 nm. ($\epsilon$ 4,500, 17,300), $\lambda_{inf}$. 285 nm. ($\epsilon$ 10,200), $\tau$ values (DMSO-$d_6$) include 1.9 (H), 2.3-3.0 (aromatic protons), 6.26 ($CH_3$). Evaporation of the mother liquors gave an isomeric mixture of methyl-2-phenyl-3-thien-2-ylpropenoates.

The cis and trans isomeric mixture of methyl 2-phenyl-3-thien-2 -yl propenoates [7.77 g.] in methanol (200 ml.) was refluxed with sodium hydroxide solution (2N : 32 ml.) for 15 minutes. The solution was cooled and the methanol removed by evaporation. The aqueous residue was diluted with water and extracted with ether. The ether extract was washed with water and dried. Evaporation gave a pale yellow oil (3.3 g.) that was dissolved in methanol (50 ml.) and refluxed with sodium hydroxide solution (2N, 13 ml.) for 52 hr. Conventional isolation of acidic material produced a pale yellow crystalline solid (2.72 g.), m.p. 115.5°–117°, $\lambda_{max}$. (EtOH) 235, 315 nm ($\epsilon$ 6,000; 19,400) $\lambda_{inf}$. 271 nm ($\epsilon$7,000), $\tau$ values (DMSO-$d_6$) include 2.68 (vinylic proton), 2.3–3.0 (aromatic protons). The spectra indicated that this material contained 10–15% of the trans-isomer. Crystallisation from an ether-petrol mixture gave a sample of the pure cis-isomer, m.p. 131°–132°.

Preparation 2

2-Thien-2-ylpent-2-enoic acid (cis isomer)

A suspension of propyl-triphenylphosphonium iodide (40 g.) in tetrahydrofuran (previously passed through a basic alumina column) (400 ml) at −10° under a stream of dry nitrogen, was treated with 1.6M butyl lithium in hexane (58 ml) at such a rate that the temperature of the mixture did not rise above −3°. The suspension was stirred at 0° when the solid dissolved giving a red solution. The solution was cooled to −10° and tert-butyl thien-2-yl-glyoxylate (18 g) in dry tetrahydrofuran (100 ml) was added to that the temperature did not rise above 0°. The brown mixture was stirred for 3 hours at 20°–23° during which time triphenylphosphine oxide was precipitated and the mixture became lighter in colour.

The suspension was evaporated to a low volume, diluted with ethyl acetate (ca 250 ml) and filtered. The filtrate was evaporated under reduced pressure to give a brown oil (25.9 g). Chromatography of the oil on silica gel (7 × 20 cm) and development with light petroleum (b.p. 60°–80°): toluene = 3:1 gave tert-butyl 2-thien-2-ylpent-2-enoate (2.1 g, 10%) as a colourless oil, $\lambda_{max}$. (ethanol) 281.5 ($\epsilon$ 7,600), $\lambda_{inf}$. 255 nm ($\epsilon$ 6,100), $\nu_{max}$ (CHBr$_3$) 1710 cm$^{-1}$ (CO$_2$R), $\tau$ values (CDCl$_3$) includes: 3.80 (triplet, CH), 7.61 (multiplet, CH$_2$CH$_3$), 8.87 (triplet, CH$_2$CH$_3$).

A solution of tert-butyl 2-thien-2-ylpent-2-enoate (1.3 g.) in anisole (0.5 ml) was treated with trifluoracetic acid (3 ml) and stirred at 23° for 5 minutes. The trifluoracetic acid was evaporated under reduced pressure and the residue dissolved in ethyl acetate. The solution was washed with 2N sodium hydroxide and the combined aqueous solutions were acidified with 2N hydrochloric acid in the presence of ethyl acetate. The aqueous phase was washed with ethyl acetate and the combined organic phases were washed with water dried and evaporated to give the title acid as a light brown oil (0.99 g, 99%), $\lambda_{max}$. 282 ($\epsilon$ 7,600, $\lambda_{inf}$. 252 nm ($\epsilon$ 5,300), $\nu_{max}$. (CHBr$_3$) 3,500, 3,100, 1728 and 1690 cm.$^{-1}$ (CO$_2$H), $\tau$ values (CDCl$_3$) include 3.50 (triplet, vinylic proton), 7.38 (multiplet, CH$_2$), 8.66 (triplet, CH$_3$).

Preparation 3

2-Thien-2-yl-5-phenylpent-2-enoic acid (cis isomer)

In a similar manner to that described in preparation 1, t-butyl $\alpha$-(diethylphosphono)-thien-2-ylacetate was treated with sodium hydride and then phenylpropionaldehyde. The isomeric mixture of esters was purified by preparative plate chromatography on silica using 2% ethyl acetate in petrol (bp.60-80) with multiple development to give t-butyl 5-phenyl-2-thien-2-ylpent-2-enoate $\lambda$max. (EtOH) 283 nm ($\epsilon$ 9,300), $\nu$max. (CHBr$_3$) 1698 cm$^{-1}$ (CO$_2$R).

The ester (0.94g.) in anisole (1ml.) was treated with trifluoracetic acid (4ml.) at 20° for 10 min. Evaporation of the trifluoracetic acid followed by conventional work up gave the title acid (0.69g.) as a yellow oil that slowly crystallised, $\lambda$max. (EtOH) 283 nm ($\epsilon$ 10,200), $\nu$max (CHBr$_3$) 3450,2600,1724 and 1690 cm$^{-1}$.

The starting material for this preparation was made as follows:

a. A solution t-butyl thien-2-ylglyoxylate (20g,) in tetrahydrofuran (100 ml.) and water (5ml.) at 0°–5° was reduced with sodium borohydride (3.0g.) for 0.5 hr. The product was isolated in ethyl acetate, dried and evaporated in the presence of a small quantity of calcium carbonate to give crystals of t-butyl 2-hydroxy-2-thien-2'-ylacetate (18.5g.) $\lambda$max. (EtOH) 237.5 nm ($\epsilon$ 7,800) $\tau$ (CDCE$_3$) values include 4.69 (2-proton) and 8150 (Bu$^t$).

The hydroxy ester (28g) in tetrahydrofuran (250 ml.) at $-5°$ was treated with calcium carbonate (Calofort U) (26g.) and phosphorus tribromide (50g.) and stirred at $-5°$ to 0° for 1 hour. The suspension was filtered and the filtrate added cautiously to a stirred cold mixture of 2N-sodium hydroxide and ethyl acetate. The product was isolated in ethyl acetate, washed with brine, dried and evaporated in the presence of a little calcium carbonate to give t-butyl 2-bromo-2-thien-2-ylacetate as a reddish oil (32g) $\lambda$max (EtOH) 244.5 nm ($\epsilon$ 5,900), $\nu$max (CHBr$_3$) 1722 cm$^{-1}$ (CO$_2$R).

The 2-bromo ester (18.2g) and triethyl phosphite (12.5 ml) were heated under reflux for 1 hr. and distilled in vacuo to give t-butyl 2-(diethylphosphono)-thien-2-ylacetate (12.9g), $\tau$ (CDCl$_3$) values include 5.30 and 5.70 (d, J 24 Hz CHP), 8.49 (s, Bu$^t$), 8.72 (t, CH$_3$). This product was contaminated with ca 50% of 0,0-diethyl-thien-2-ylphosphonate, $\tau$ (CDCl$_3$) values include 6.46 and 6.80 (d,J 21 Hz, CH$_2$P). The presence of this decarboxylated impurity was allowed for in Preparation 3.

Preparation 4

2-Thien-2-ylbut-2-enoic acid (cis isomer)

In a similar manner to that described in Preparation 2, ethyl triphenylphosphonium bromide was treated with n-butyl lithium and t-butyl thien-2-ylglyoxylate to give, after chromatography, t-butyl 2-thien-2-ylbut-2-enoate $\lambda$max (EtOH) 280 nm ($\epsilon$ 8,000), $\nu$max (CHBr$_3$) 1705 cm$^{-1}$(CO$_2$R). Deprotection with trifluoracetic acid in anisole for 10 min. at 23° give the title acid as an oil which solidified on cooling, $\tau$ (CDCl$_3$, 60 MHz) values include 3.37 (q,J 7Hz, vinyl proton), 7.86 (d, J 7Hz, CH$_3$).

Preparation 5

3-Phenyl-2-fur-2-yl-propenoic acid (cis isomer)

Benzyl triphenyl phosphonium chloride (29.00g) was added to potassium t-butoxide (8.90g) in anhydrous t-butanol (200 ml) and the solution stirred at room temperature for 30 min. t-Butyl fur-2-ylglyoxylate (11.00g) in t-butanol (25 ml) was added slowly with stirring and the mixture kept overnight at room temperature. The solvent was evaporated at reduced pressure, the residue extracted with petrol, the portion soluble in petrol recovered and purified by chromatography on a silica-gel column. Elution with toluene/petrol mixture (2:1) gave the t-butyl ester of the title compound as an oil, $\nu$max (CHBr$_3$) 1710 (CO$_2$Bu$^t$) and 730 cm$^{-1}$ (C$_6$H$_5$), $\tau$ (DMSO.d6; 60 MHz) 2.24, 3.40, 3.52 (furyl protons), 2.60 (phenyl protons), 2.89 (vinyl proton) and 8.52 (t-butyl protons).

The t-butyl ester (2.06g), anisole (28 ml) and trifluoracetic acid (20 ml) were stirred for 8 min at room temperature. Ether was added, the solution washed with water and evaporated at reduced pressure. Toluene was added and evaporated, and the residue, dissolved in ether, was extracted with aqueous sodium bicarbonate solution. The aqueous extract was acidified with 2N hydrochloric acid and extracted with ether. The ethereal solution was washed with water, dried over sodium sulphate and evaporated, giving an oily residue which was recrystallised from cyclohexane to give the title compound $\lambda$max. (EtOH) 228,316.5 nm ($\epsilon$ 7,900; 21,500), $\tau$ (d6-DMSO; 60 MHz) 2.20,3.36,3.42 (fur-2-yl protons), 2.89 (vinylic proton).

Preparation 6

3-(4-Cyanophenyl)-2-thien-2-yl propenoic acid (cis isomer)

In a similar manner to that described in preparation 5, 4-cyanobenzyltriphenylphosphonium chloride was treated with potassium t-butoxide and t-butyl fur-2-ylgyloxylate to give, after chromatography, t-butyl 3-(4-cyanophenyl)-2-thien-2'-ylpropenoate (cis isomer) $\lambda$max. (EtOH) 246,270 and 331 nm and 331 nm ($\epsilon$8,650; 22,100), $\nu$max (CHBr$_3$) 2222 (CN) and 1700 cm$^{-1}$(CO$_2$R), $\tau$ (d$_6$-DMSO; 60 MHz) values include 2.81 (vinylic proton and 8.54 (Bu$^t$). Deprotection with trifluoracetic acid in anisole gave the title acid, $\tau$ (d$_6$-DMSO; 60 MHz) values include 2.10, 2.35 (4-cyanophenyl protons), 2.35, 2.6–3.0 (m, fur-2-yl protons) and 2.90 (vinylic proton).

The phosphonium salt used for this preparation was made as follows:- a solution of triphenylphosphine (39.3g) and 4-chloromethylbenzonitrile (22.7g) in toluene (400 ml) was heated under reflux for 53 hr. After cooling, the solid was collected, washed with toluene and dried to give 4-cyanobenzyltriphenylphosphonium chloride (35.4g), $\nu$max (nujol) 2230 (CN) and 1436 cm.$^{-1}$ (PPH$_3$), $\tau$ (d$_6$-DMSO; 60 MHz) values include 2.0–2.5 (aromatic protons), 4.47 (CH$_2$).

Preparation 7

3-Fur-2-yl-2-thien-2-yl-propenoic acid (cis isomer)

A mixture of thien-2-ylacetic acid (15.00g), furfuraldehyde (9.61g), triethylamine (16 ml) and acetic anhydride (32 ml) was heated for 8 hr under reflux under an atmosphere of nitrogen, cooled and added to water (2 liters). The mixture was made alkaline with potassium hydroxide, heated with charcoal (1g) on a water-bath for 2 hr, filtered, cooled and acidified with 5N hydrochloric acid. The solution was extracted with ethyl acetate, the organic extract dried over sodium sulphate and evaporated, giving a mixture of the cis- and trans-isomers of 3-fur-2-yl-2-thien-2-yl-propenoic acid. Trituration with a small volume of ether gave a solid which was recrystallised three times from acetonitrile, giving the title compound m.p. 194°–195.5° C, $\lambda$max. 244, 335 nm ($\epsilon$ 5,250; 23,100 $\tau$ ($d_6$-DMSO; 60 MHz) values include 3.20 (vinylic proton).

Preparation 8

4-Methoxy-2-phenylbut-2-enoic acid (cis-isomer)

To a solution of 4-hydroxy-2-phenylbut-2-enoic acid lactone (Swain, G., Todd, A.R; Waring, W.S., J.Chem. Soc. 1944, 548) (5g) in 2N sodium hydroxide (300 ml) was added dimethylsuphate (100 ml) over 4 hours. The pH was maintained at 14 by the addition of 2N sodium hydroxide. After stirring for 16 hours the reaction was washed with ether, acidified with 2N hydrochloric acid and extracted with ethyl acetate. The organic extracts were extracted with sodium bicarbonate solution and the aqueous extracts were washed with ethyl acetate, acidified with 2N hydrochloric acid and extracted with ethyl acetate. The organic extracts were dried and the solvent evaporated to leave an oil which was stirred with ether to give the title acid as a white solid (1.9g), m.p.112.8°, $\lambda$max. 250 nm ($\epsilon$ 9,700), $\tau$ ($d_6$-DMSO) values include 3.70 (t, J 6 Hz, vinylic proton), 5.69 (d,J6 Hz, $CH_2$), 6.67 (s, $CH_3$).

Preparation 9

4-Acetoxy-2-phenylbut-2-enoic acid (cis isomer)

To 2N sodium hydroxide (75 ml) was added Z-4-hydroxy-2-phenylbut-2-enoic acid lactone (1.5 g) in portions with stirring and warming to about 50°. The solution was cooled in an icebath and treated, dropwise with stirring, with acetic anhydride (15 ml). After twenty minutes, the solution was acidified (2N HCl) to pH 1 and extracted with ethyl acetate. The combined extracts were shaken with saturated aqueous sodium bicarbonate solution, and the combined aqueous extracts were washed with ethyl acetate, then acidified (2N hydrochloric acid) and extracted with ethyl acetate. The combined extracts were dried evaporated to give an oil which was dried under vacuum to give the title acid (0.5g), $\lambda$max (EtOH) 251 nm ($\epsilon$ 6,500), $\nu$max. ($CHBr_3$) 1785 $cm^{-1}$ (OCO $CH_3$), $\tau$ ($d_6$-DMSO) values include 2.95 (ph), 3.70 (vinylic protron), 5.02 ($CH_2$) 7.90 ($CH_3$).

Preparation 10 t-butyl fur-2-ylglyoxylate

Fur-2-ylglyoxylic acid (12.5g) and liquid isobutylene (ca 25 ml) were added to a cooled stirred solution of sulphuric acid (10 ml) in anhydrous ether (100 ml) and the solution was kept at 3° C for 3 days. Ether (150 ml) was added, the solution washed with aqueous sodium bicarbonate solution until free from acid, dried over sodium sulphate and evaporated, giving a brown oil. The oil was distilled at 76°–82° C/0.3 mm, giving t-butyl fur-2-ylglyoxylate (11.6g) $\lambda$max (EtOH) 233 ($\epsilon$2,080) and 286 nm ($\epsilon$11,700), $\nu$max ($CHBr_3$) 1718 ($CO_2Bu^t$) and 1664 $cm^{-1}$ (—C-CO-), $\tau$ (DMSO-$d_6$; 60 MHz) 1.80, 2,32, 3.15 (furyl protons) and 8.41 ($Bu^t$).

Preparation 11 t-butyl thien-2-ylglyoxylate

In a similar manner to that described in preparation 10,thien-2-ylglyoxylic acid was converted into its t-butyl ester, $\lambda$max (EtOH) 272 and 296.5 nm ($\epsilon$ 6,900; 7,950), $\nu$max ($CHBr_3$) 1716 ($CO_2Bu^t$), $\tau$($CDCl_3$) 1.86,2.12, 2.74 (thien-2-yl protons), 8.34 ($Bu^t$).

EXAMPLE 1

Sodium (6R,7R)-3-Acetoxymethyl-7-7-(2-phenyl-3-thien2-ylpropenamido) ceph-3-em-4-carboxylate (cis isomer)

2-Phenyl-3-thien-2-ylpropenoic acid (cis isomer) (690 mg.) (Preparation 1) in dry methylene chloride (20 ml.), containing dimethylformamide (1 drop) was treated at room temperature with oxalyl chloride (0.29 ml.) for 8 hr. Evaporation gave an orange gum that was stored at 0°. The prepared acid chloride in dry methylene chloride (15 ml.) was added dropwise to a solution of (6R,7R)7-aminocephalosporanic acid (816 mg.) and triethylamine (1.02 ml.) in dry methylene chloride (40 ml.) and stirred at room temperature for 4 hour.

The solvent was removed by evaporation and the residue partitioned between ethyl acetate and water. The aqueous phase was acidified and extracted with ethyl acetate to give a solid (1.23 g.) that was dissolved in acetone (20 ml.) and treated with a solution of sodium 2-ethylhexanoate (498 mg.) in acetone (5 ml.). The resulting precipitate was collected, washed with acetone and dried to give the title compound (840 mg.) $\lambda_{max}$ (pH 6 buffer) 263, 320 nm ($\epsilon$15,300, 19,200)$\lambda_{inf.}$ 241 nm. ($\epsilon$13,600 ), $\tau$ values (DMSO-$d_6$) include 2.4 (vinylic proton), 2.2–2.9 (aromatic protons), 0.31 (-NH-).

EXAMPLE 2

Sodium (6R,7R)-3-Acetoxymethyl-7-(2,3-diphenyl-propenamido) ceph-3-em-4-carboxylate (cis isomer)

2,3-Diphenylpropenoic acid (cis isomer) [448 mg.] was converted into the acid chloride and used to acylate (6R,7R)-7-aminocephalosporanic acid as described in Example 1 giving the title salt as a white powder (240 mg) $\lambda_{max}$. (pH 6 buffer) 272 nm ($\epsilon$ 18,600) $\lambda_{inf.}$ 290 nm. ($\epsilon$16,200 ), $\tau$ values (DMSO-$d_6$) include 2.92 (vinylic proton), 2.2–2.8 (aromatic protons), 0.4 (—NH—).

EXAMPLE 3

Sodium (6R,7R)-3-Acetoxymethyl-7-(3-phenyl-2-thien-2yl-propenamide) -ceph-3-em-4-carboxylate (cis isomer)

A solution of sodium methoxide in methanol (2.88 ml., 1.3 N) was added to a solution of 3-phenyl-2-thien-2-ylpropenoic acid (cis isomer) (Das et al., J.Med.-Chem., 1972, 15, 370) (0.86 g.) in methanol (10ml.). The dried solid obtained after evaporation of the methanol was suspended in benzene (20 ml.) containing dimethylformamide (2 drops) and treated with oxalyl chloride (0.275 ml.). After stirring at room temperature for 1 hr. the mixture was evaporated to an oil, suspended in acetone (10 ml) and added at 0° to a solution of (6R,7R)-7-aminocephalosporanic acid (0.85 g.) in acetone (10 ml.) and water (10 ml.) containing anhydrous sodium carbonate (0.34 g.). The solution was stirred at room temperature for 2 hr. The acetone was removed by evaporation and the aqueous solution was washed with ethyl acetate, then acidified to pH 2 under a layer of ethyl acetate and the product isolated by further extraction with the same solvent. The combined, dried extracts were evaporated to a yellow foam which was redissolved in ethyl acetate and treated with a solution of sodium 2-ethylhexanoate (0.47 g.) in the same solvent (10 ml.). After 1 hr. at 0° the solid was collected, thoroughly washed with ethyl acetate and ether and dried to give the title salt, (0.88 g.), $[\alpha]_D^{23} + 72°$ (C 1.02, $H_2O$), $\lambda_{max.}$ (pH 6 buffer) 228, 260, 315 nm ($\epsilon$15,950; 16,400; 16,600), $\tau$(DMSO-$d_6$) values include 0,35 (NH), 3.08 (vinylic proton), 7.99 ($OCOCH_3$).

EXAMPLE 4

(6R,7R)-3-(Benzothiazol-2-yl) thiomethyl-7-(3-phenyl2-thien-2-yl-propenamido) ceph-3-em-4-carboxylic acid (cis isomer)

Diphenylmethyl (6R,7R)-7-amino-3-(benzothiazol-2-yl) thiomethylceph-3-em-4-carboxylate hydrochloride salt, (1.426 g.) was partitioned between ethyl acetate (30 ml.) and sodium bicarbonate solution (3% w/v; 30 ml). The organic layer was separated, dried and treated with 3-phenyl-2-thien-2-yl-propenoic acid (cis isomer) 561 mg) and N,N-dicyclohexylcarbodiimide (530 mg.) and the solution stirred at 22° for 45 hrs. The reaction was cooled to 0°, filtered and the filtrate washed successively with 2N-hydrochloric acid, water, sodium bicarbonate solution, water, dried and the solvent removed in vacuo to give the crude diphenylmethyl ester of the title compound (1.831 g.)

The above ester (1.7 g.) was dissolved in anisole (3 ml.) and treated with trifluoroacetic acid (12 ml.). After 15 min. at 21°, the reagents were removed in vacuo and the residue partitioned between ethyl acetate and sodium bicarbonate solution. The aqueous solution was washed with more ethyl acetate and the combined organic layers dried and the solvent removed in vacuo. The resulting oil was triturated with ether to give the title carboxylic acid as a buff powder (350 mg.), $[\alpha]_D$ −292° (C 0.1, DMSO). $\lambda_{max.}$ (EtOH) 321 nm ($\epsilon$29,800); $\lambda_{inf.}$ 255 nm ($\epsilon$13,400), $\nu_{max.}$ (nujol), 3310 (N-H), 1752 ($\beta$-lactam), 1650 and 1520 $cm^{-1}$ (CONH) $\tau$(DMSO-$d_6$) values include 0.26 (d, J 9; NH), 3.04 (s; vinylic proton), 4.20 (dd; J 9.5; 7-H), 4.80 (d; J 5: 6-H).

EXAMPLE 5

(6R,7R)-3-(5-Methyl-1,3,4-thiadiazol-2-yl) thiomethyl-7(3-phenyl-2-thien-2-yl propenamido) ceph-3-em-4carboxylic acid (cis isomer)

A solution of diphenylmethyl (6R,7R)-7-amino-3-(5methyl-1,3,4-thiadiazol-2-yl) thiomethylceph-3-em-4carboxylate (2.637 g.) in dry dichloromethane (45 ml.) was treated with 3-phenyl-2-thien-2-yl propenoic acid (cis isomer) (1.177g.) and N,N-dicyclohexylcarbodiimide (1.085 g.) and stirred at 25° for 48 hrs. The solution was cooled to 0°, filtered, and the filtrate washed successively with aqueous sodium bicarbonate, water, dilute hydrochloric acid, water, and dried and the solvent removed in vacuo to give the crude diphenylmethyl ester of the title compound (1.952 g., after chromatography). The above ester (1.661 g.) was dissolved in anisole (3 ml.) and trifluoroacetic acid (12 ml.) added. The reaction was allowed to proceed at 20° for 15 min. and the reagents were removed in vacuo. The residue was partitioned between ether and aqueous sodium bicarbonate solution, and the ether layer extracted with more bicarbonate solution. The combined aqueous layers were washed with ether, adjusted to pH 1.9 and extracted with ethyl acetate. The combined extracts were washed with water, dried and the solvent removed in vacuo. The resulting froth was triturated with ether to give the title compound as a pink amorphous solid (500 mg.), $[\alpha]_d$-251° (C 0.2, DMSO), $\lambda_{max.}$ (pH 6 buffer) 272 nm ($\epsilon$18,050), $\nu_{max.}$ (mujol), 1772 ($\beta$-lactam), 1656, 1500 (CONH). $\tau$(DMSO-$d_6$), values include 0.24 (d, J 9, NH), 3.03 (s; vinylic proton), 4.12 (dd, J 9, 5, 7-H) 4.75 (d, J5, 6-H), 7.28 (s,$CH_3$).

EXAMPLE 6

(3S, 5R, 6R)-6-(3-Phenyl-2-thien-2-yl propenamido)2,2-dimethypenam-3-carboxylic acid (cis isomer)

A solution of sodium methoxide in methanol (2.88 ml., 1.3N) was added to a solution of 3phenyl-2-thien-2-ylpropenoic acid (cis isomer) (0.86 g.) in methanol (10 ml.). The dried solid obtained by evaporation was suspended in benzene (20 ml.) containing dimethylformamide (2 drops) and oxalyl chloride (0.275 ml.) was added. After stirring at room temperature for 1 hr. the mixture was evaporated to an oily solid which was suspended in acetone (10 ml.) and added at 0° to a solution of (3S, 5R, 6R)-6-amino-2,2-dimethylpenam-3-carboxylic acid (0.7 g.) in acetone (10 ml.) and water (10 ml.) containing anhydrous sodium carbonate (0.34 g.). The solution was stirred at room temperature for 2 hr. The acetone was removed by evaporation and the solution washed with ethyl acetate. The aqueous layer was covered with ethyl acetate and acidified to pH 2 and the penicillanic acid was isolated in the usual way as a foam (1.06 g.). This material was dissolved in ether (10 ml.) and added dropwise to petroleum spirit (b.p. 40°–60°) (75 ml.). The title compound was collected by filtration as a yellow solid (0.81 g.) $[\alpha]_D^{19}$ + 187° (c 0.82 dioxan), $\lambda_{max.}$ (pH 6 buffer) 315 nm. ($\epsilon$8,825), $\tau$(DMSO-$d_6$) values include 0.49 (—NH), 3.08 (vinylic proton), 8.46, 8.54 (gem methyl groups), $\lambda_{max.}$ (nujol) 1776 ($\beta$-lactam).

EXAMPLES 7–14

General Procedure for the preparations of Sodium (6R,7R)-3-Acetoxymethyl-7-(2-aryl-3-substituted propenamido) ceph-3-em-4-carboxylates (cis-isomers).

A solution of the appropriate 2-aryl-3-substituted propenoic acid (cis isomer) in dry benzene or methylene chloride containing a few drops of dry N,N-dimethylformamide was treated with triethylamine (1 equiv.) and then with oxalyl chloride (1.0–1.2 equiv.). The reaction mixture was stirred at room temperature for 0.75–2 hr. and then evaporated under reduced pressure. The residual acid chloride was dissolved in dry methylene chloride and added to a solution of (6R,7R)-7-aminocephalosporanic acid (1 equiv.) in dry methylene chloride containing triethylamine (2 equivs.). The mixture was stirred at room temperature for 1–3 hr. then washed successively with 2N-hydrochloric acid and water, dried and evaporated to dryness. The residue in ethyl acetate was washed several times with saturated aqueous sodium hydrogen carbonate. The combined aqueous phases were covered with ethyl acetate and acidifed to pH 1–2 with 2N-hydrochloric acid. The organic phase was washed with water, brine, dried and evaporated. The resulting foam was dissolved in acetone and treated with a 10% solution of sodium 2-ethylhexanoate in acetone (approx. 1 equiv.) to give the sodium salt which was collected and dried. Products so obtained are listed in Table 1:

lactam), $\tau$ ($d_6$-DMSO, 100 MHz) include 0.36 (NH), 3.10 (vinylic proton) and 4.32 (7-H).

EXAMPLE 16

N-[(6R,7R)-7-(3-phenyl-2-thien-2-yl-propenamido)-ceph-3-em-3-ylmethyl]-pyridinium-4-carboxylate.(cis isomer)

(6R,7R)-3-Acetoxymethyl-7-[3-phenyl-2thien-2-yl-propenamido]-ceph-3-em-4-carboxylic acid(cis isomer) (4.07 g) was added to a solution of sodium iodide (14.25 g) and pyridine (4.0 ml) in water (44 ml) at 80° C and the mixture stirred for 1 hr. The mixture was diluted with water to about 100 ml. and filtered to remove undissolved solid. The filtrate was evaporated under reduced pressure at < 40° C to small volume, treated with two drops of methylisobutyl ketone and Table 1

| Eg. No. | A | B | $[\alpha]_D$ (solvent) | $\lambda$ max.$^{nm}$ (solvent) | $\epsilon$ | $\beta$-lactam $\nu$max. cm$^{-1}$ (solvent) | $\tau$ values at 100 MH$_z$ | | | |
|---|---|---|---|---|---|---|---|---|---|---|
| | | | | | | | solvent | x | y | z |
| 7 | thienyl | CH$_3$CH$_2$— | +82° (H$_2$O) | 261 (H$_2$O) | 15,500 | 1754 (CH Br$_3$) | D$_2$O | — | 3.82 | 4.22 |
| 8 | thienyl | CH$_3$ | +83° (H$_2$O) | 257.5 (H$_2$O) | 14,800 | 1750 (Nujol) | d$_6$-DMSO | 0.62 | 3.89 | 4.30 |
| 9 | thienyl | thienyl | +44° (H$_2$O) | 263 (H$_2$O) | 15,300 | 1752 (Nujol) | D$_2$O | — | — | 4.12 |
| 10 | furyl | Ph— | +103° (DMSO) | 231.5 258 317 (pH 6 buffer) | 14,800 13,700 17,500 | 1750 (Nujol) | d$_6$-DMSO | 0.30 | 2.97 | 4.26 |
| 11 | thienyl | furyl | +53° (DMSO) | 260 337 (pH 6 buffer) | 13,250 24,300 | 1750 (Nujol) | d$_6$-DMSO | 0.43 | 3.22 | 4.22 |
| 12 | thienyl | CN-phenyl- | +55° (DMSO) | 253.5 332.5 (pH 6 buffer) | 18,300 18,300 | 1754 (Nujol) | d$_6$-DMSO | 0.24 | 2.16 | 4.28 |
| 13 | thienyl | PhCH$_2$CH$_2$ | +83° (H$_2$O) | 263 (H$_2$O) | 15,800 | 1760 (Nujol) | d$_6$-DMSO | 0.59 | 3.99 | 4.34 |
| 14 | Ph | CH$_3$ | +79.5° (DMSO) | 244 | 14,180 | 1772 (Nujol) | d$_6$-DMSO | 0.70 | 3.82 | 4.16 |

EXAMPLE 15

Sodium (6R,7R)-3-Carbamolyoxymethyl-7-(3-phenyl-2thien-2-ylpropenamido)-ceph-3-em-4-carboxylate (cisisomer).

The acid chloride prepared as described in Example 3 was used to acylate (6R,7R)-7-amino-3-carbamoyloxymethylceph-3-em-4-carboxylate in a similar manner to give the title salt, $[\alpha]_D^{20}$ + 96° (c. 0.8 DMSO), $\lambda_{max}$ (pH 6 buffer) 231.5, 261 and 317 nm ($\epsilon$ 14,800; 15,400, 17,800) $\nu$max (nujol) 1750 cm$^{-1}$ ($\beta$- acidified to pH2 with 2N hydrochloric acid. The yellow precipitate of the hydriodide was collected and suspended in water. The suspension was adjusted to pH4, filtered, and the residue shaken with a mixture of water (20 ml), methylene chloride (20 ml) and Amberlite LA-2 resin (2 ml). The aqueous layer was separated, evaporated under reduced pressure < 40° C and the residue washed with methylene chloride giving the title compound $[\alpha]_D^{23}$ + 29.8° (c 0.15 in DMSO) $\lambda_{max}$ (pH 6 buffer) 227 ($\epsilon$, 15,000), 258 ($\epsilon$, 16,300) 316 nm ($\epsilon$ 14,800), $\lambda_{max}$ (nujol) 1760 cm$^{-1}$ ($\beta$-lactam) $\tau$ (d$_6$-DMSO, 100 Hz) values include 0.38 (NH), 3.13 (vinylic proton), 4.30 (dd, 7-H).

EXAMPLE 17

(6R,7R)-3-Acetoxymethyl-7-[4-acetoxy-2-phenylbut-2-enamido]ceph-3-em-4-carboxylic acid (cis isomer)

To a solution of 4-acetoxy-2-phenylbut-2-enoic acid (cis isomer) (0.42 g) in toluene (20 ml) was added dimethylformamide (4 drops) followed by triethylamine (0.32 ml). To the stirred solution was added oxalyl chloride (0.18 ml) and the reaction was stirred for twenty minutes at room temperature, then stripped to dryness. The residue was dissolved in acetone (10 ml) and added dropwise with stirring to a solution of (6R,7R)-3-acetoxymethyl7-aminoceph-3-em-4-carboxylic acid (0.68 g) and sodium bicarbonate (0.3 g) in water (15 ml). The resulting solution was stirred for two hours, washed with ethyl acetate, acidified with 2N hydrochloric acid and extracted three times with ethyl acetate. The combined extracts were dried (sodium sulphate), concentrated and added dropwise with vigorous stirring to petroleum (200 ml). The precipitate was filtered, washed and dried to give the title compound 10.15g; 17%), $\lambda_{max.}$ (pH 6 buffer) 251.5 nm ($\epsilon$12,800), $\nu_{max}$ (nujol) 1774 cm$^{-1}$ ($\beta$-lactam), $\tau$ (d$_6$-DMSO; 100 MHz) values include 0.56 (d, J 8.5 Hz, NH), 3.79 (t, J6Hz, vinyl proton), 4.16 (dd, J8, 5 H$_2$, 7-H).

EXAMPLE 18

(6R,7R)-3-Acetoxymethyl-7-(4-methoxy-2-phenylbut-2-enamido)ceph-3-em-4-carboxylic acid (cis-isomer)

A solution of dicyclohexylcarbodiimide (0.82 g) and (Z) 4-methoxy-2-phenylbut-2-enoic acid (cis isomer) 1.39g) in methylene chloride (40 ml) was stirred at room temperature for thirty minutes then filtered and evaporated to dryness. The residue was taken up in acetone (20 ml) and added with vigorous stirring to a solution of (6R,7R)-3-acetoxymethyl-7-amino-ceph-3-em-4-carboxylic acid (3.9 g) and sodium bicarbonate (1.81 g) in water (60 ml). The reaction was stirred at room temperature for five hours, then washed twice with ether, acidified (2N hydrochloric acid) and extracted three times with ethyl acetate. The combined extracts were dried, concentrated and added dropwise with vigorous stirring to petroleum (250 ml.). The precipitate was collected and dried to give the title compound (0.44 g, 27%), [$\alpha$]$_D$ +54° (c 0.75 DMSO), $\lambda_{max.}$ 249.5 nm ($\epsilon$14,735), $\nu_{max.}$ 1780 cm$^{-1}$ ($\beta$-lactam), $\tau$ (d$_6$-DMSO, 100 MHz) values include 0.61 (d,NH) 3.80 (vinylic proton) 4,16 (dd, 7-H).

EXAMPLE 19

(2S; 5R, 6R)-6-(2-phenylbut-2-enamido)-2,2-dimethylpenam-3-carboxylic acid (cis-isomer).

In a similar manner to that of Example 17, 2-phenylbut-2-enoic acid (cis isomer) was converted into its acid chloride and coupled with (3S, 5R, 6R)-6-amino-2,2-dimethylpenam-3-carboxylic acid to give the title compound, $\lambda_{max.}$ (pH 6 phosphate buffer) 234, 345 nm ($\epsilon$7,2000; 4,260), $\nu_{max.}$ (nujol) 1770 ($\beta$-lactam), $\tau$ (d$_6$-DMSO) values include 0.92 (d, NH), 3.83 (q, 6Hz vinyl proton), 4.3–4.5 (m, 5 and 6 H), 8.42 and 8.52 (gem dimethyl).

EXAMPLE 20

(3S, 5R, 6R)-6-(3-phenyl-2-fur-2-yl-propenamido)-2,2-dimethylpenam-3-carboxylic acid (cis-isomer)

In a similar manner to that of Example 17 3-phenyl-2-fur-2-yl -propenoic acid (cis isomer) was used to prepare the title compound, $\lambda_{max}$ (pH 6 phosphate buffer), 315 nm ($\epsilon$ 16,930), $\nu_{max.}$ (CHBr$_3$) 1780 cm$^{-1}$, $\tau$ (d$_6$-DMSO; 100 MHz) values include 0.54 (d,NH), 3.04 (vinylic proton), 8.47 and 8.53 (gem dimethyl).

We claim:

1. A 7$\beta$-acrylamidoceph-3-em-4-carboxylic acid of the formula:

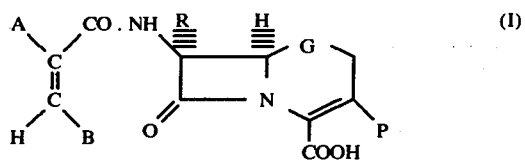

wherein A is phenyl; naphthyl; thenyl; furyl; optionally substituted by a cyano group; B is a group as defined for A; or alkyl, alkenyl or alkynyl of up to 7 carbon atoms or said alkyl, alkenyl or alkynyl substituted by a group as defined for A, C$_{1-4}$ alkoxy, or D$_{1-4}$ acyloxy; R is hydrogen; G is > S; P is a group of the formula -CH$_2$Y wherein Y is -O.CO.R$^d$, wherein R$^d$ is C$_{1-7}$ alkyl; C$_{1-7}$ alkyl substituted by cyano, carboxy, C$_{1-4}$ alkoxycarbonyl, hydroxy, carboxycarbonyl, chlorine, bromine, iodine or amino; C$_{2-7}$ alkenyl; phenyl; phenyl substituted by hydroxy; chloro; fluoro, methyl, nitro, amino, methoxy or methylthio; thienyl; pyridyl; cyclohexyl; cyclopentyl; cyclopropyl; sydnone; naphthyl or 2-ethoxynaphthyl; or -O.CO.Q.R$^d$ wherein R$^d$ is as defined above, or hydrogen and Q is O, S or NH; or a physiologically acceptable salt thereof.

2. The compound of claim 1 which is (6R,7R)-3-carbamoyloxymethyl-7-[3-phenyl-2-thien-2-yl propenamido] ceph-3-em-4-carboxylic acid (cis isomer).

3. The compound of claim 1 which is (6R,7R)-3-)benzothiazol-2-yl)-thiamethyl-7-[3-phenyl-2-thien-2-yl propenamido] ceph-3-em-4-carboxylic acid (cis isomer).

4. The compound of claim 1 which is (6R,7R)-3-acetoxymethyl-7-[3-fur-2-yl-2-thien-2-ylpropenamido] -ceph-3-em-4-carboxylic acid (cis isomer).

5. The compound of claim 1 which is (6R,7R)-3-acetoxymethyl-7-[4-methoxy-2-phenylbut-2-enamido]ceph-3-em-4-carboxylic acid (cis isomer).

6. The compound of claim 1 which is (6R,7R)-3-acetoxymethyl-7-[3-phenyl-2-thien-2-yl propenamido] ceph-3-em-4-carboxylic acid (cis isomer).

7. A 7$\beta$-acrylamidoceoph-3-em-4-carboxylic acid of the formula:

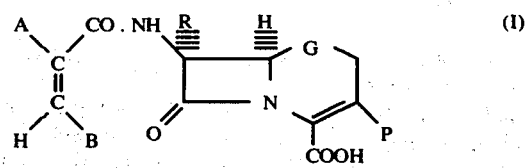

wherein A is phenyl; phenyl substituted by cyano; thienyl or furyl group, B is as defined for A or may also be a $C_{1-7}$ alkyl group optionally substituted by a group as defined for A, $C_{1-4}$ alkoxy or $C_{1-4}$ acyloxy, R is hydrogen; G is >S; P is a group of the formula —$CH_2Y$, wherein Y is -O.CO.$R^a$, wherein $R^a$ is $C_{1-7}$ alkyl; $C_{1-7}$ alkyl substituted by cyano, carboxy, $C_{1-4}$ alkoxycarbonyl, hydroxy, carboxycarbonyl, chlorine, bromine, iodine or amino; $C_{2-7}$ alkenyl; phenyl; phenyl substituted by hydroxy, chloro, fluoro, methyl, nitro, amino, methoxy or methylthio; thienyl, pyridyl; cyclohexyl; cyclopentyl; cyclopropyl; sydnone, naphthyl or 2-ethoxynaphthyl; or —O.CO.Q.$R^d$ wherein $R^d$ is as defined above, or hydrogen and Q is O, S or NH; and a physiologically acceptable salt of a compound of formula I.

* * * * *